United States Patent [19]

Schrevel et al.

[11] Patent Number: 5,290,688

[45] Date of Patent: Mar. 1, 1994

[54] METHOD FOR INTENSIVE, IN VITRO CULTURE OF *BABESIA DIVERGENS* STRAINS

[75] Inventors: Joseph Schrevel, Lussac-les-Chateaux; André Gorenflot, Gif-sur-Yvette; Eric Precigout, Poitiers; Alain Marchand, Carquefou; Philippe Brasseur, Rouen; Monique L'Hostis, Nantes; Daniel Rigomier; Alexis Valentin, both of Poitiers; Emmanuel Vidor, Lyons; Guy Bissuel, Le Bois-d'Oingt Chanrion, all of France

[73] Assignee: Rhone Merieux, Lyons, France

[21] Appl. No.: 752,625

[22] PCT Filed: Dec. 20, 1990

[86] PCT No.: PCT/FR90/00934

§ 371 Date: Oct. 17, 1991

§ 102(e) Date: Oct. 17, 1991

[87] PCT Pub. No.: WO91/08771

PCT Pub. Date: Jun. 27, 1991

[30] Foreign Application Priority Data

Dec. 20, 1989 [FR] France ................. 89 16890

[51] Int. Cl.$^5$ .................. C12N 1/10; C12N 1/28; C12P 21/00; A61K 39/00
[52] U.S. Cl. ..................... 435/7.1; 435/70.4; 435/947; 435/249; 435/258.1; 424/88
[58] Field of Search ................. 435/70.4, 71.1, 240.31, 435/258, 947; 424/88; 530/350

[56] References Cited

U.S. PATENT DOCUMENTS

| | | | |
|---|---|---|---|
| 4,055,466 | 10/1977 | Torney et al. | 435/240.31 |
| 4,457,915 | 7/1984 | Goodger et al. | 422/88 |
| 4,596,707 | 6/1986 | Ristic et al. | 424/88 |
| 4,767,622 | 8/1988 | Ristic et al. | 424/88 |
| 4,777,036 | 10/1988 | Laurent | 422/88 |

FOREIGN PATENT DOCUMENTS 0018579 of 0000 European Pat. Off. .
2200638 8/1988 United Kingdom .

OTHER PUBLICATIONS

C. M. Winger et al., "A monoclonal antibody-derived antigen of *Babesia divergens*: characterization and investigation of its ability to protect gerbils against virulent homologous challenge", Parasitology, vol. 99, 1989, pp. 341–348.

C. M. Winger et al., "A monoclonal antibody to *Babesia divergens* which inhibits merozoite invasion", Parasitology, 94, 1987, pp. 17–27.

*Primary Examiner*—Christine M. Nucker
*Assistant Examiner*—Chris Dubrule
*Attorney, Agent, or Firm*—Wegner, Cantor, Mueller & Player

[57] ABSTRACT

Method for the culture of *Babesia divergens*, characterized in that the Babesia strain is maintained under culture in a culture medium free from serous protein but containing lipoproteins and red blood corpuscles, and a method for preparing exoantigens and a vaccine containing these antigens.

11 Claims, 5 Drawing Sheets

METHOD FOR INTENSIVE, IN VITRO CULTURE OF *BABESIA DIVERGENS* STRAINS

The present invention was made at the Cell Biology Laboratory of POITIERS University, Unité de Recherche Associée au Centre National de la Recherche Scientifique (National Centre for Scientific Research Associated Research Unit), no. 290, and at the Parasitology Laboratory of Rhône Mérieux.

The present invention relates to a process for the intensive in vitro culture of Babesia divergens and for preparing exoantigens and parasite proteins, and to their use as a vaccine.

Babesioses, also known as piroplasmoses, are intraerythrocytic parasitoses which are common in domestic and wild animals (cattle, dogs, horses, rodents, in particular) and rarer in man (16 clinical cases in Europe and approximately 200 in the USA have been described since 1957). They are transmitted by haematophagous acarines (ticks) and, in relevant cases, by blood transfusion in man.

There is a large number of Babesia species.

Among the various animal babesioses, bovine babesiosis caused by *B. bovis* (=*B. argentina*), *B. bigemina*, *B. major* and *B. divergens* is the most important from an economic standpoint.

In Europe, bovine babesiosis due to *B. divergens* causes limited mortality as a result of effective chemotherapy (for example imidocarb). However, cases of chemoresistance are beginning to be observed, especially in France (National Veterinary School, Nantes). On the other hand, the morbidity of the infection is a source of substantial economic losses.

In the developing countries, bovine babesiosis represents a major obstacle to increasing the productivity of cattle rearing and one of the main causes of economic losses recorded in some regions of Africa.

There are several methods of controling Babesia:
control of the arthropod vectors (ticks),
curative or preventive antiparasitic chemotherapy,
vaccination of animals against Babesia: at the present time, only vaccines against bovine babesiosis due to *B. bovis* and to *B. bigemina* (Australia, Latin America, Israel, South Africa) and against canine babesiosis due to *B. canis* (France) are used on a large scale; there is still no vaccine on the market against *B. divergens* and *B. major*, the species responsible for bovine babesiosis in Europe; only Taylor has proposed a vaccine obtained from blood of parasitised cattle (GB-A-2,200,638). Among anti-Babesia vaccines described, there are two major types: live vaccines and inactivated vaccines (their advantages and drawbacks are summarised in Table 1).

The parasite exoantigens collected in culture supernatants have already been used for vaccination against bovine babesiosis due to *B. bovis* and is *B. bigemina* (EP-0,018,579 B1) and canine babesiosis due to *B. canis* (EP-0,220,988 A1).

TABLE 1

| Vaccine Type | Reproducibility | Ease of commercial exploitation | Potential risk of infection | Risk of rekindling the virulence of the strain | Risk of erythrocyte isoimmunisation | Efficacy of the vaccine |
|---|---|---|---|---|---|---|
| LIVE VACCINES: | | | | | | |
| a) "Premunisation" (infection followed by chemotherapy) | poor | no | yes | yes | low | good |
| b) Irradiated parasites | poor | no | ? | ? | low | good |
| c) Attenuated parasites (rapid passages in animals) | variable | no | yes | yes | low | good |
| INACTIVATED VACCINES: | | | | | | |
| Prepared from infected cattle: | | | | | | |
| a) Particulate antigens | poor | no | no | no | high | low |
| b) Soluble antigens extracted from paracitised red cells lysis supernatants | poor / good | no / yes | no / no | no / no | high / low | low / good |
| c) soluble plasma antigens | poor | no | no | no | low | low |
| Prepared from in vitro cultures: | | | | | | |
| Soluble exoantigens isolated from culture supernatants | good | yes | no | no | low | good |

The present invention relates more especially to a process for preparing exoantigens and proteins enabling a vaccine to be obtained against bovine babesiosis due to *B. divergens*, and which may be extended to other Babesia species.

The process for the culture of Babesia is characterised in that the Babesia strain is maintained in culture on a culture medium free from serum protein but containing lipoproteins as well as red cells.

The lipoproteins which are usable according to the present invention are preferably of natural origin, in particular of human origin.

Among these lipoproteins, high density lipoprotein, hereinafter designated "HDL", should be mentioned more especially.

The indices of multiplication of *Babesia divergens* in culture in vitro in semi-defined medium are comparable to those obtained with complex media containing from 5 to 10% of human serum.

This new technique may be adapted to the in vitro culture of other Babesia species such as *B. bovis, B. bigemina, B. canis, B. equi, B. major* and *B. microti.*

The use of semi-defined medium enables the exoantigens present in the medium to be purified and has advantages for the culture of Babesia:
- reduced risk of contamination of the laboratory workers by the possible presence of viruses in the sera (hepatitis virus, HIV);
- good reproducibility of the growth of the parasites, which is no longer dependent on the variability of serum batches; and
- elimination of the problems of serum/red cell incompatibility and possibility of using all red cells of the ABO system.

This semi-defined medium based on lipoproteins preferably contains HDL fractions at a concentration of between 0.2 and 5 mg in lipid/ml, especially 0.5 and 3 mg in lipid/ml with the addition or otherwise of LDL at a concentration of between 0.5 and 1.5 mg in lipid/ml. This medium can also contain growth factors such as bovine insulin at a concentration of between 0.5 and 10 µg/ml, human transferrin at a concentration of 10 to 200 µg/ml, selenium and betacyclodextrin.

These culture media free from serum protein are known. An example of such media is RPMI 1640, used for cell cultures. These media are in general supplemented with serum proteins, in particular with foetal calf serum; in the present case, the supplement consists of lipoproteins.

These media are known to those skilled in the art and will not be described further. The terminology of equivalents to RPMI 1640 medium will sometimes be used for these media.

This culture process enables Babesia exoantigens, in particular, to be prepared, the exoantigens being isolated from the culture medium.

*B. divergens* produces exoantigens in the culture supernatant, some of which induce immunoprotection in vaccinated animals. The use of semi-defined medium enables parasite antigens which are candidates for the stimulation of humoral and/or cell-mediated immunity to be collected, by eliminating the problems linked to the presence of major plasma proteins (albumin, immunoglobulin) in the culture medium. The process enables a higher concentration of the antigen to be produced while good solubility of the latter is preserved. It likewise improves the purification of the protective serum factors.

In the case of *B. divergens* and *B. canis*, the collection of antigens hitherto met with the difficulties of maintaining continuous cultures by the methods previously described. Thus, during the culture of *B. canis* used for the Pirodog vaccine (Rhône Mérieux), the parasitaemia level falls below 1% in the course of three weeks (Moreau Y. and Laurent N., In: "Malaria and Babesiosis", Ristic M., Ambroise-Thomas P., Kreier J. P. (eds), Martinus Nijhoff, Dordrecht, Holland, 1984, 132). This situation hence gave rise to the need to initiate further cultures regularly with red cells of parasitised dogs.

The lower levels of parasitaemia, described in the literature, obtained during the culture of *B. divergens* in bovine red cells and the use of high concentrations of bovine serum do not permit either the accumulation of large amounts of parasite antigens in the culture supernatants or a ready separation of the vaccinating protein fraction; these antigens are present in very small amounts in the supernatant compared with the bovine serum proteins.

The *B. divergens* strain cultured according to the process of the invention, and in particular on human red cells, since June 1987, does not require a daily change of medium for parasitaemia levels below 5%. Since the culture in question is of the continuous type, it is not necessary to initiate cultures regularly with blood of parasitised cattle of gerbils.

The *B. divergens* exoantigens obtained by these culture processes may be purified, concentrated and analysed after labelling with radioactive amino acids. The interference caused by serum proteins during the separation of the parasite proteins can thus be demonstrated.

Analysis by gel filtration (Superose 12 column, FPLC, Pharmacia) enables three groups of radiolabelled parasite proteins to be detected in the supernatants originating from semi-defined media, whereas the same experiment carried out in the presence of complete medium (10% serum) shows a single major peak of radioactivity due to an accumulation caused by the presence of serum proteins.

The soluble proteins of the *B. divergens* supernatant which confer protection against infection have the following relative molecular masses: 31-33 kDa (doublet), 35-37 kDa (doublet), 43±2 kDa, 46±3 kDa, 50±2 kDa, 66-68 kDa (doublet), 70±3 kDa, 80±3 kDa, 90±3 kDa, 110±3 kDa, 130±3 kDa, 140±5 kDa and 150 kDa.

The present invention relates, in addition, to the fractions of *B. divergens* exoantigens having a KaV:
- fraction 1) of between 0 and 0.27,
- fraction 2) of between 0.27 and 0.57,
- fraction 3) of between 0.57 and 0.78,
- fraction 4) of between 0.78 and 0.95, and especially fractions 2 and 4.

The invention also relates to the antigenic proteins of which these fractions are composed, and in particular the protein of molecular weight 17,000 ±2,000 Da appearing in fraction 4.

This is a protein which is found in both *B. divergens* and *B. canis*. It is an exoantigen for which the corresponding antibody has an inhibitory power of 100% at a concentration of 50 µg/ml. This protein is present on the surface of mitochondrial type structures as well as on the membranes.

The p35 protein of molecular weight 35,000±2,000 Da is a palmitoylated exoantigen glycoprotein which does not cross with *B. canis* and which occurs in fractions 3 and 4.

The p50 protein of molecular weight 50,000±3,000 Da in fractions F3 and F4 is recognised by the serum of protected animals, cattle and gerbils.

The culture technique according to the invention in human red cells or in bovine red cells is usable for an industrial production in semi-automated systems employing large volumes of culture media. The exoantigens originating from the supernatant of these cultures in semi-defined medium are usable for obtaining vaccinating fractions.

These fractions may be used mixed with immunity adjuvants, in particular adjuvants of the lipid type and/or saponins, for example.

Although it is more especially advantageous to use the fractions described above in the vaccinating strategy, in particular fractions 3 and 4, it is possible to use one or more purified proteins or alternatively proteins obtained by other methods, in particular by genetic recombination.

Various antigens can be isolated and used to produce immunosera and/or monoclonal antibodies.

These antibody fractions may be used in therapy or alternatively for diagnostic purposes. The monoclonal antibodies may also be used to fractionate the culture supernatants and purify the exoantigens by known processes.

The present invention also relates to these various antigen and antibody fractions for use both in therapy and in prevention and/or diagnosis.

Other features and advantages of the present invention will become apparent on reading the examples below.

In the drawings appended to the present description.

A: in the HDL fraction, the apoproteins A4, E, A1 and A2 are detected, human serum albumin (HSA) is present in variable amounts depending on the preparation of the HDL fraction.

B: in the LDL fraction, the apoprotein B-100 is preponderant.

EXAMPLE 1

Conditions of Continuous Culture of *B. divergens* in Human Red Cells a) *B. divergens* strains

The *B. divergens* strain used in the present vaccination strategy is a human strain collected at Rouen in June 1987, and maintained since then in culture in vitro on human red cells. It will be designated *B. divergens* strain Rouen 1987. Naturally, it is possible to use other strains, this one being mentioned only by way of a specific example.

Any bovine strain of *B. divergens* may be cultured in human red cells by initially preparing a mixed culture comprising bovine red cells/human red cells or gerbil red cells/human red cells. In the latter case, the parasitised gerbil blood originates from gerbils infected either with fresh (or cryopreserved) parasitised bovine blood or, equally well, with fresh (or cryopreserved) parasitised gerbil blood.

Several hundred bovine strains collected in France in the regions affected by *B. divergens*, cryopreserved in liquid nitrogen after prior passages in gerbils, have been gathered at Nantes National Veterinary School (A. Marchand).

b) Continuous culture medium

Its composition is as follows:

| | |
|---|---|
| RPMI 1640: | 10.4 g |
| NaHCO$_3$: | 2.1 g/l |
| HEPES: | 8.3 g/l |
| H$_2$O q.s. | 900 ml |

The pH is adjusted to 7.3 (7.2–7.4).

100 ml of human serum decomplemented by heating to 56° C. for 30 minutes, and optionally gentamicin (0.1 to 1 mg/l), are then added.

DMEM, MEM or any equivalent synthetic medium may be used in place of RPMI 1640.

The medium is then filtered through a 0.22 μm filter. The human serum used is a mixture of sera of healthy subjects of different or identical blood groups in the ABO system (serologically virus-negative).

Decomplemented bovine sera, selected beforehand for their non-agglutination of 0+ red cells, may also be used.

This is the continuous culture medium (RPMI+10% human serum) in which the human strains isolated at Rouen and at Le Mans have been maintained since June 1987 and May 1988, respectively.

c) Red cells

The red calls used are human red cells, usually of group O+, but culturing of *B. divergens* can also be carried out in red cells of any other blood group of the ABO system. In the latter case, while it is preferable to use a compatible serum, the use of incompatible sera is nevertheless possible since agglutination of the red cells does not inhibit the growth of the parasite.

The human blood samples, collected under sterile conditions on anticoagulants of the ACD (citric acid, sodium citrate, dextrose) or equivalent type, may be used for the culture for a maximum period of 7 days. Before culturing, the red cells are washed twice in RPMI 1640, then once in RPMI 1640+10% serum+gentamicin. The final centrifugation pellet of washed red cells is used for the culture.

d) Culture condition

Irrespective of the size of the culture dishes, the haematocrit is between 2 and 5%. Care should be taken, in addition, that the volume of the red cell culture is suited to the area of the culture dish; by way of example, 5 ml of culture having a 2–5% haematocrit for a conventional 25 cm$^2$ culture dish.

Culturing of *B. divergens* is performed at 37° C.:
dish closed after gassing with a ternary gaseous mixture: N$_2$: 91%, O$_2$: 6%, CO$_2$: 3%.

dish open in a bell jar: $CO_2$: of the order of 5%
dish open in a $CO_2$ incubator: 5%.

Starting with a 1% parasitaemia level, these culture conditions enable parasitaemia levels of 30 to 80% to be attained regularly after 3 to 5 days of culture, respectively. The true rate of multiplication per 24 hours is in the region of 5 with strain *B. divergens* strain Rouen 1987.

No change of medium is necessary before the parasitaemia level reaches 5%. A change is performed every 24 hours for parasitaemia levels of between 5 and 30%. Two changes of medium every 24 hours are carried out when the parasitaemia level reaches 30%. The culture supernatants having a parasitaemia level of between 20 and 40% are collected: they form the basis of the proposed vaccine.

A subculturing of the human strain (Rouen 1987) of *B. divergens* every 5 days has enabled it to be maintained in continuous culture since June 1987.

EXAMPLE 2

In vitro culture of *B. divergens* in semi-defined media based on lipoproteins and growth factors a) Preparation of the lipoproteins and growth factors The lipoproteins are prepared, starting with human serum from healthy donors, by differential ultracentrifugation according to the technique described by Havel et al., (1955, J. Clin. Exp. Invest., 34, 1345-1353). The density of the serum separated after simple coagulation of the blood without an additive (blood harvested in dry bottles) is adjusted successively to 1.019, 1.063 and 1.210 g/ml by adding KBr in the presence of EDTA (0.1% final). Three successive centrifugations of 22 hours at 120,000 g will enable 3 fractions to be isolated:

| | |
|---|---|
| Very Low Density Lipoprotein (VLDL) | 1.006–1.019 g/ml |
| Low Density Lipoprotein (LDL) | 1.019–1.063 g/ml |
| High Density Lipoprotein (HDL) | 1.063–1.210 g/ml |

The LDL and HDL fractions used for the culture are dialysed at 4° C. for 24 hours, first against saline solution buffered to pH 7.4 with 5 mM Tris-HCl, then against a solution comprising RPMI 1640, 17 mM sodium bicarbonate, 25 MM HEPES (pH 7.4). The solutions obtained are sterilised by filtration through a 0.22#m filter and stored at 4° C. The quantity of lipoproteins is estimated after colorimetric protein assay (Lowry et al., 1951, J. Biol. Chem., 193, 265-275) multiplying this value by 2 for HDL and by 4 for LDL; it is, in effect accepted that the protein contents of HDL and LDL are 50 and 25%, respectively, of the final mass (Patsch et al., 1974, J. Lip. Res., 15, 356-366). The apoprotein composition of the isolated fractions is monitored by electrophoresis on 15% acrylamide gel (SDS-PAGE).

b) Semi-defined medium permitting at least 2 growth cycles

The culture medium for the in vitro growth of *B. divergens* strain Rouen 1987 on human red cells should comprise a mixture of HDL, LDL and growth factors added to RPMI 1640 medium or equivalent media, 25 mM HEPES, 17 mM $NaHCO_3$; the pH is adjusted to 7.4. This base medium may be supplemented by adding antibiotics.

Figure 1A:
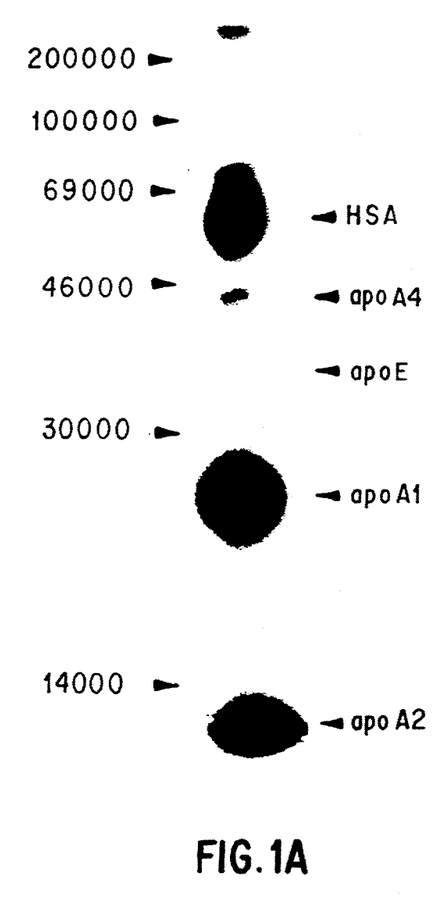
FIGS. 1A and 1B show the autoradiograph of the proteins of the HDL (FIG. 1A) and LDL (FIG. 1B) fractions labelled with iodine-125 according to McFarlane (1958)
Figure 1B:
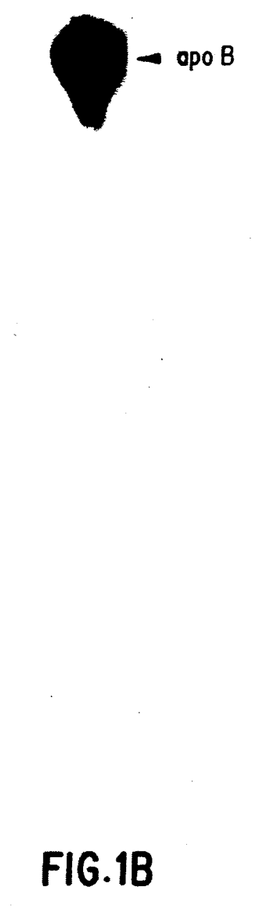
Figure 2A:
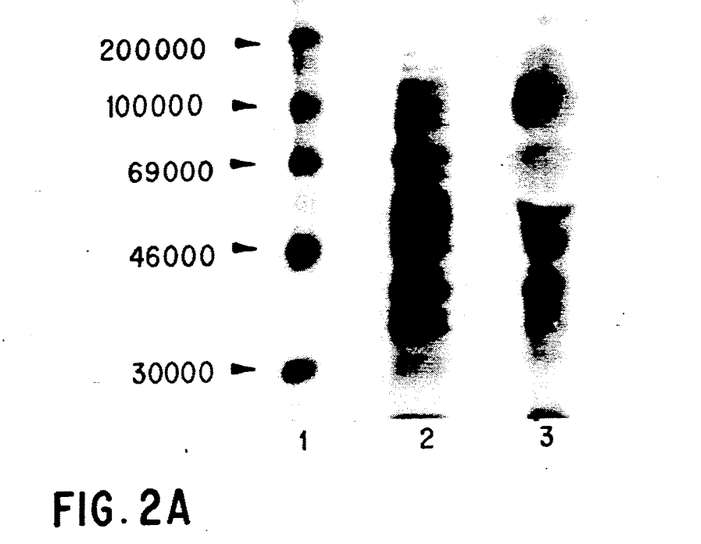
FIG. 2A shows the SDS-PAGE (10% acrylamide) electrophoresis of the supernatant of in vitro culture of *B. divergens* labelled metabolically with [$^{35}$S]methioninee, 1: molecular weight kit
2: supernatant of culture in semi-defined medium (H+L)
3: supernatant of culture in serum-containing medium (10% human serum)
Figure 2B:
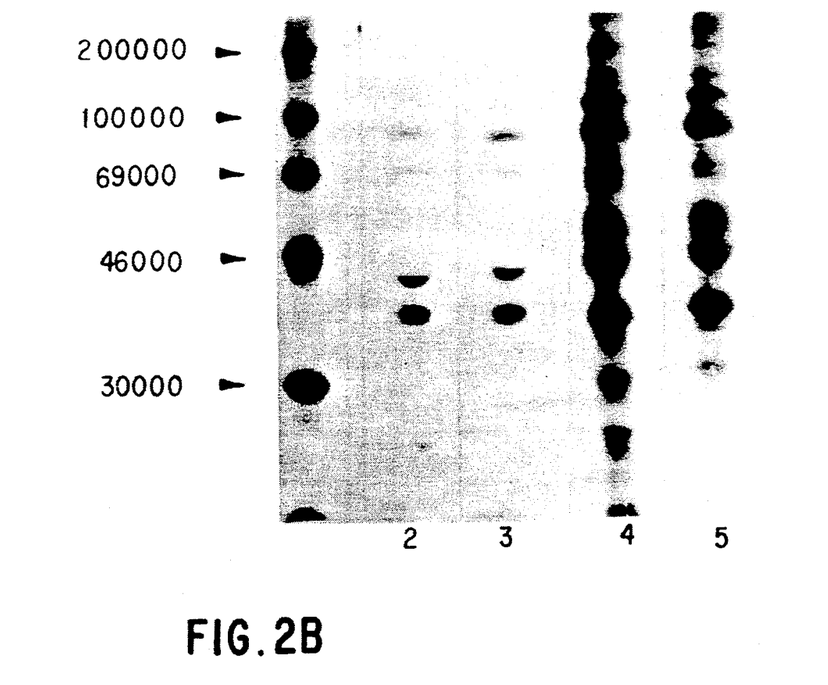
FIG. 2B shows the immunoprecipitation of in vitro culture of [$^{35}$S]methioninee-labelled *B. divergens* with an immune human serum, 1: molecular weight kit
2: supernatant of culture in serum-containing medium (10% human serum)
3: supernatant of culture in semi-defined medium (H+L)
4: *B. divergens* total antigens in serum-containing medium (10% human serum)
5: *B. divergens* total antigens in semi-defined medium (H+L)
Figure 3A:
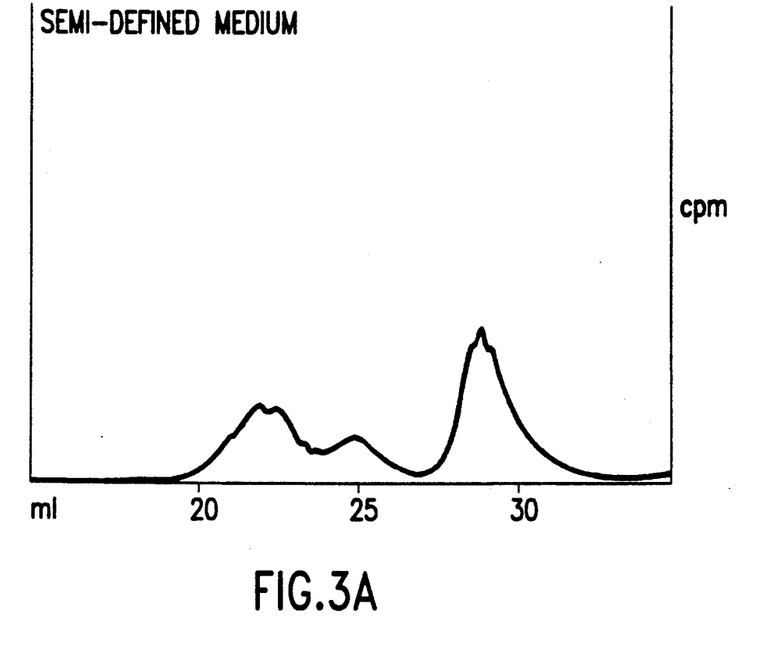
FIGS. 3A and 3B show the separation by gel filtration (Superose 12 column, Pharmacia) of the parasite antigens present in the culture supernatant of [$^{35}$S]methioninee-labelled *B. divergens;*
Figure 3B:
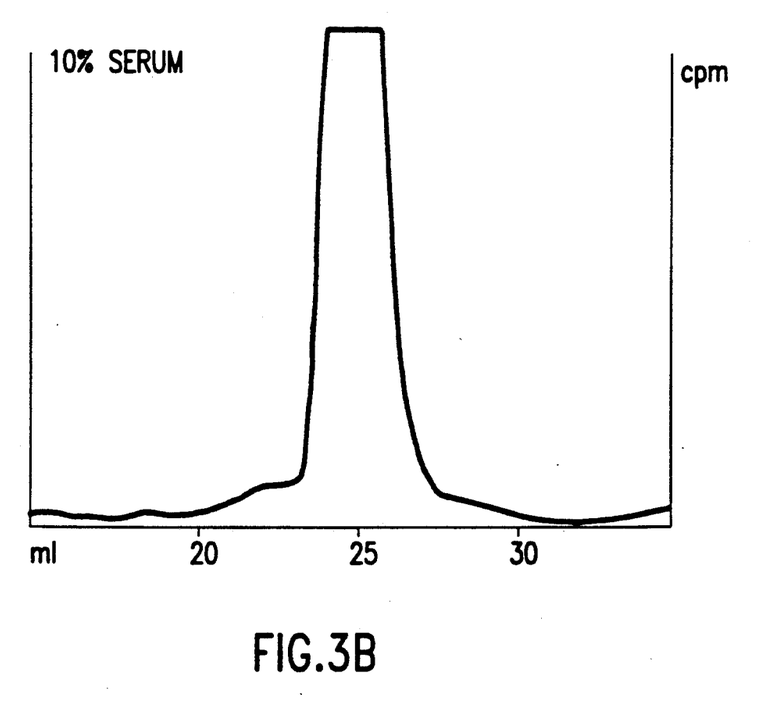
Figure 4:
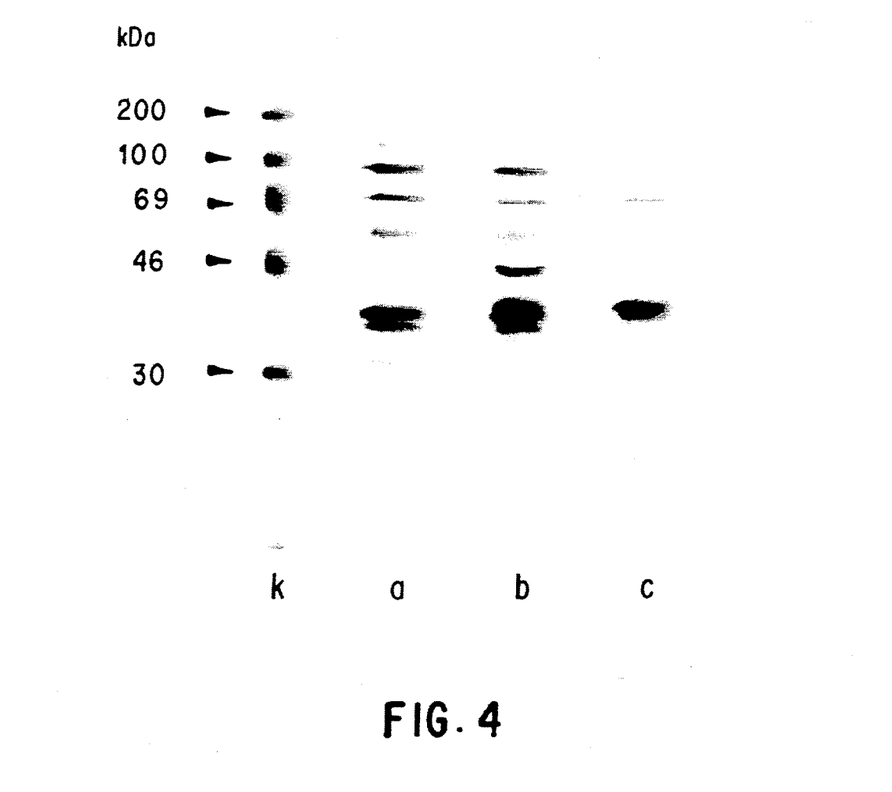
FIG. 4 illustrates the immunoprecipitation of *B. divergens* cultures labelled metabolically with [$^{35}$S]methioninee.
Figure 5:
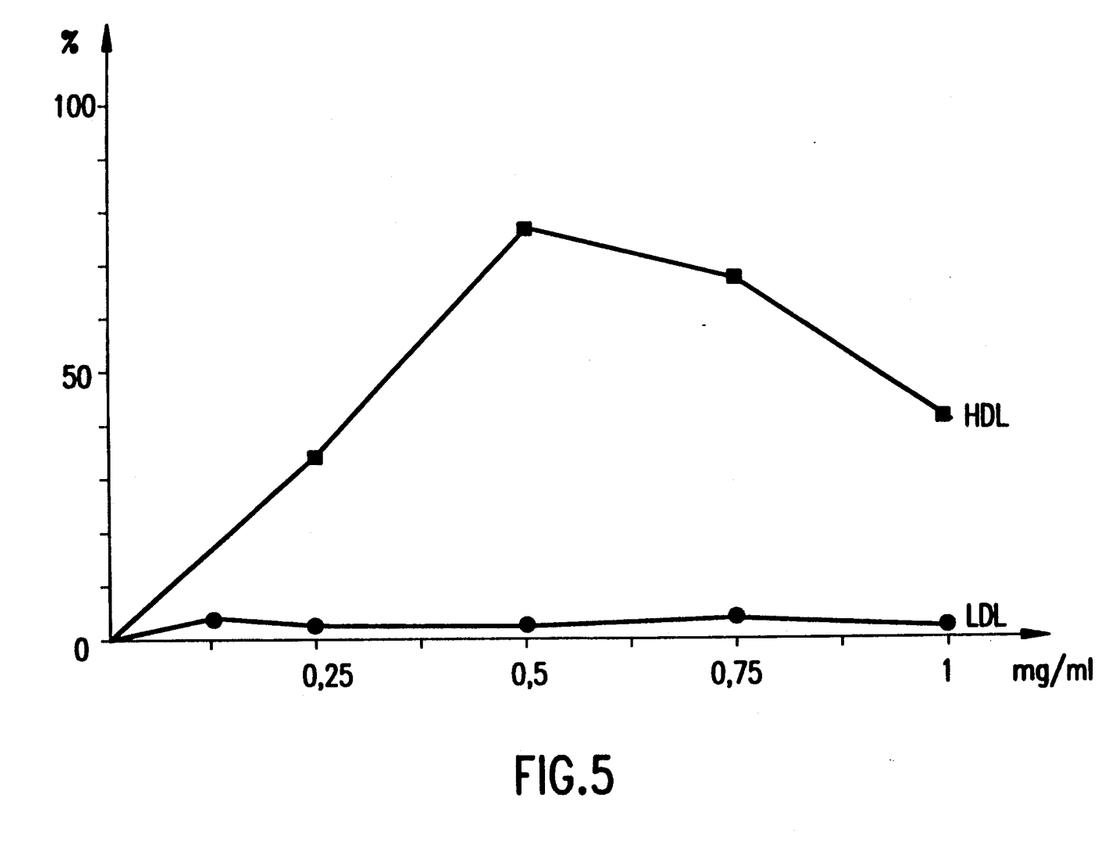
FIG. 5 illustrates the growing of *B. divergens* in a semi-defined medium containing various concentrations in lipoproteins (HDL or LDL) compared with growing observed in a medium containing 10% of human serum (growing 100%).

The total HDL fraction of human origin (d=1.063–1.210 g/ml) used contains in general the apoproteins AI 28 kDa, AII 17.4 kDa, AIV 45 kDa and C 6.6-8.8 kDa, and serum albumin in an amount which varies according to the preparation of the total HDL fraction. The proteins of the HDL fraction may be labelled specifically with iodine-125 according to the technique of McFarlane (1958, Nature, 182, 53) and detected by SDS-PAGE and autoradiography (FIG. 1A). This HDL fraction is used at concentrations of between 0.5 mg and 2 mg/ml for an initial parasitaemia level of the order of 1%. The apoprotein concentration of the total LDL in the medium is between 0.5 and 1.5 mg/ml, and the above iodine-125 technique according to McFarlane shows a predominant labelling of the apoprotein B-100 (FIG. 1B).

Human transferrin and bovine insulin are used at doses of 100 μg/ml (10–200 μg/ml) and 1 μg/ml (0.5–10 μg/ml) respectively. The index of multiplication, defined as the ratio of the parasitaemia level after reinvasion to the initial parasitaemia level, was determined on the various *B. divergens* strains cultured in 25cm² dishes. The incubations tested related to six stages of reinvasion, which enables it to be ensured that the parasites are still viable at the 6th biological cycle after being set up in culture in semi-defined medium.

TABLE 2

Index of multiplication between the time of setting up in culture (T0) and the 24th hour of culture (T24), and the period T24 to 48 hours (T48) (H, HDL, L, LDL)

| | INDEX OF MULTIPLICATION | |
|---|---|---|
| | T0-24 | T 24-48 |
| Serum | 4 | 4 |
| HL | 4,1 | 2,8 |

In vitro cultures using HDL and LDL with the addition of 50 μg/ml transferrin, 10 μg/ml selenium and 250 μg/ml beta-cyclodextrin were also prepared. These factors possess properties of stimulating cultures (selenium: peroxidation inhibitor; beta-cyclodextrin: inhibitor of the toxicity of molecules present in the culture medium). Indices of multiplication similar to the above were obtained.

For high initial parasitaemia levels (15 to 20%), the indices of multiplication in the HL semi-defined medium are similar to the reference serum-containing medium during the first 20 hours, equivalent to 2 erythrocytic growth cycles of *B. divergens* (the multiplication cycle of *B. divergens* cultured in vitro on human red cells is, in effect, of the order of 8 to 10 hours.

These culture conditions enable soluble parasite proteins, and in particular exoantigens, to be purified.

c) Simplified semi-defined medium for obtaining proteins secreted during a biological cycle The semi-defined medium containing only the total HDL fraction at a concentration of 1 mg in lipid/ml enables the parasite proteins liberated during the different stages of the erythrocytic cycle and at the time of reinvasion to be collected, in particular after metabolic labelling of the parasite using radioactive amino acid(s).

This medium hence permits good maturation of *B. divergens;* it would be possible to collect the antigens produced during this maturation and to concentrate them under favourable conditions characterised by the absence of plasma proteins in the culture medium.

EXAMPLE 3

Production and purification of *B. divergens* proteins stimulating humoral immunity and/or cell-mediated immunity a) Metabolic labelling and production of parasite proteins

The in vitro cultures of *B. divergens* on human red cells are incubated with 40 μCi/ml of [$^{35}$S]-L-methionine (Amersham; more than 1 Ci/μmol) in RPMI 1640 or equivalent medium without methionine, to which the constituents of the semi-defined media are added. Other radioactive amino acids may be used, such as [$^{3}$H]-L-isoleucine (0.1 Ci/μmol) and [$^{3}$H]-L-histidine (0.05 Ci/μmol). The culture media containing the parasite proteins secreted into the medium or liberated during reinvasion of the red cells by the merozoites are centrifuged (600 g for 5 min) and then filtered on 0.22 μm Millex filters to remove the particulate constituents. The proteins are then concentrated from 5- to 10-fold by ultrafiltration across membranes (B15 or PM10 Centricon, Amicon). The parasite proteins are analysed by SDS-PAGE electrophoresis followed by autoradiography.

b) Separation of the parasite proteins

The parasite proteins radiolabelled with one or more amino acids may be fractionated by conventional techniques of liquid chromatography (ion exchange, gel filtration, isoelectric focusing, hydrophobic nature, and the like), combined with a determination of their radioactivity by a counter of the "Flow-one", model CR (Radiomatic, Tampa USA) type. The purified parasite protein fractions can contain the proteins of the HDL fraction, but are depleted of the many native or modified serum proteins of the host which are liable to interfere with the immune reaction (humoral and/or cell-mediated).

c) Identification of the soluble parasite proteins of *B. divergens*

The supernatants of in vitro culture of *B. divergens* on human red cells in the present of [$^{35}$S]-L-methionine, concentrated by ultrafiltration, show modifications of electrophoretic migration in complete medium (10% serum) for the proteins from 40 to 70,000 (FIG. 2A). The soluble proteins of the *B. divergens* culture supernatant which confer protection against infection can be visualised by metabolic labelling with [$^{35}$S]methionine. They have the following relative molecular masses: 31-33 kDa (doublet), 35-37 kDa (doublet), 43±2 kDa, 46±3 kDa, 50±2 kDa, 66-68 kDa (doublet), 70±3 kDa, 80±3 kDa, 90±3 kDa, 110±3 kDa, 130±3 kDa, 140±5 kDa and 150 kDa. Among the latter, the most immunogenic, visualised by immunoprecipitation in all the isolates tested, have molecular masses varying from 34 to 37 kDa, from 43 to 46 kDa, from 69 to 72 kDa and from 90 to 100 kDa. The interference caused by serum proteins during the separation of the parasite proteins may be confirmed by liquid chromatography. The supernatants of an in vitro culture of *B. divergens* (8% parasitaemia level), radiolabelled for 12 hours with [$^{35}$S]-L-methionine, may be separated by gel filtration (Superose 12 column, FPLC, Pharmacia) after filtration (0.22 μm). Three groups of radio labelled parasite proteins are detected in the supernatants originating from semi-defined media with the Flow-one, model CR radioactivity counter (FIG. 3). The same experiment carried out in the presence of complete medium (10% serum) shows a single major peak of radioactivity due to an accumulation caused by the presence of serum proteins (FIG. 3).

The antigenic natures of the parasites cultured in normal medium or in semi-defined media are similar, both as regards the total proteins and as regards the soluble proteins of the parasite, as shown by the immunoprecipitation experiments carried out with the same immune serum (FIG. 2B).

EXAMPLE 4

Identification of the immunogenic proteins of *B. divergens* from in vitro culture on human red cells, essential to the development of a vaccine, necessitated a study of the immune response to *B. divergens* in three receptive hosts: ox, man, gerbil. For this study, the following immune sera were used:

- immune human sera: these were 5 sera originating from French patients, and especially the patient treated successfully at Rouen in June 1987.
- immune gerbil sera: gerbils were infected experimentally with *B. divergens* strain Rouen 1987 with $10^8$ parsitised red cells/animal, then treated with imidocarb (Carbesia N.D. Lab. Coopers) when the parasitaemia level reached 5% and finally infected with the same strain on several occasions from the following month onwards. The animals thus treated were protected against *B. divergens* and designated by the name hyperimmune gerbils.
- immune calf sera: a splenectomised calf (referred to as V1) received successively $10^{11}$ parasitised red cells of the Rouen patient (*B. divergens* strain Rouen 1987) and then $10^{10}$ red cells of gerbils parasitised by the same strain (the red cells of the cured patient could no longer be used).

A splenectomised calf (referred to as V2) received on two occasions $10^{10}$ red cells of gerbils parasitised by the same strain.

1) Identification of the immunogenic proteins of *B. divergens* in lysates of varasitised red cells using immune bovine, gerbil and human sera A metabolic labelling of *B. divergens* (strain Rouen 1987) cultured in vitro on human red cells was performed according to conventional methods using [$^{35}$S]methionine with incubation times of 12 hours. The proteins immunoprecipitated by means of the patient's sera collected from day D4 of the clinical episode up to the 9th month following were analysed by SDS-PAGE electrophoresis in a reducing medium and autoradiographed.

Antibodies directed towards the 35 kDa protein group are the first to appear.

A communal antigenic identity, in particular with the major protein and minor protein groups, is observed irrespective of the immune serum used.

FIG. 4 illustrates the immunoprecipitation of *Babesia divergens* cultures labelled metabolically ([$^{35}$S]-methionine) with different immune sera derived from:

a: gerbil
b: human
c: ox
(k=molecular weight kit).

2. Immunoprecipitations of the parasite proteins resent in *B. divergens* (strain Rouen 1987) cultured supernatants using three immune sera (human, gerbil, calf)

After removal of the serum immunoglobulins by binding to protein A-*Staphylococcus* or protein A-Sepharose CL 4B (Pharmacia), the culture supernatants were immunoprecipitated using the above three immune sera (human, gerbil, calf). These immunoprecipitations enabled major proteins possessing the same electrophoretic mobility in SDS-PAGE/reducing medium to be demonstrated in the three hosts (30 to 100 kDa), as well as minor proteins possibly possessing a molecular weight above 100 kDa and below 30 kDa.

EXAMPLE 5

Purification of *B. divergens* exoantigens

The *B. divergens* Rouen 1987 culture supernatants It (parasitaemia level 30–40%) obtained in semi-defined medium (HDL : 0.5 mg/ml, LDL : 0.125 mg/ml, expressed as mg of the lipoprotein proteins) by the process described above were concentrated 15-fold on Amico CF25 and loaded onto a Superose 12 column (Pharmacia FPLC system). Using 25 mM ammonium acetate buffer, pH 7.3, the various fractions are eluted at a flow rate of 0.3 ml/min. The various fractions obtained are:

Fraction I: F1: 6.5 to 11 ml elution volume
Fraction II: F2 : 11 to 16.5 ml elution volume
Fraction III: F3 : 16.5 to 20 ml elution volume
Fraction IV: F4 : 20 to 23 ml elution volume.

Table 3 summarises the KaV values of these various fractions, as well as the molecular masses of the antigens contained in each of these fractions, obtained by spreading on SDS-PAGE gel.

TABLE 3

| | Characteristics of the fractions | | | |
|---|---|---|---|---|
| | F1 | F2 | F3 | F4 |
| Elution Volume (ml) | 6.5–11 | 11–16.5 | 16.5–20.1 | 20.1–23 |
| KaV | 0–0.27 | 0.27–0.57 | 0.57–0.78 | 0.78–0.95 |
| MM | 136 | 136 | 189 | 189 |
| SDS-PAGE (kDa) | 124 | 124 | 101 | 33 |
| | 97 | 101 | 88 | 28 |
| | 92 | 90 | 76 | 25 |
| | 86 | 88 | 64 | 24 |
| | 69 | 84 | 52 | 18 |
| | 66 | 72 | 35 | 15 |
| | 57 | 64 | 28 | |
| | 53 | 63 | 26 | |
| | 49 | 57 | 25 | |
| | 37 | 49 | 24 | |
| | 29 | 43 | 22 | |
| | | 35 | 20 | |
| | | 33 | 18 | |
| | | 26 | 16 | |
| | | 24 | 14 | |
| | | 21 | | |
| | | 16 | | |

Column: Superose 12 HR 10/30 (Pharmacia)
Culture supernatant concentrated 50-fold on Centriflo CF25 (Amicon)
$Kav = (Ve - Vt)/(Vt - Vo)$
Ve: elution volume
Vt: column volume
Vo: dead volume

EXAMPLE 6

Anti-*B. divergens* vaccine

1) Vaccinating antigens

Vaccination is carried out using as antigens the parasite exoantigens and proteins collected in the supernatant of in vitro culture of *B. divergens* on human red cells when the parasitaemia level is of the order of 30 to 40%. The supernatant used as a vaccine corresponds to cultures containing approximately $10^8$ parasitised red cells per ml of medium. The culture medium containing the parasite antigens is centrifuged at 1,500 g and then filtered under sterile conditions through a 0.22 μm filter. The dose of vaccinating antigen may be adapted to the animal to be vaccinated by means of the usual processes for concentrating proteins. To the dose of parasite proteins contained in 0.2 ml in the case of the gerbil, a corresponding volume of saponin at a concentration of 1 mg/ml of RPMI 1640 is added as an adjuvant to obtain a final saponin concentration of 0.5 mg/ml. The use of other adjuvants is possible.

2) Use of semi-defined culture media for the collection of parasite exoantigens and proteins The semi-defined medium described above makes it possible to collect the parasite exoantigens and proteins with a very low contamination with serum proteins, and possesses a definite advantage compared with earlier patents (for example, the culture medium of Ristic (USA) contains 30 to 50% of serum; that of Canning (GB) 40%).

This medium will bring about a substantial improvement in the concentration and fractionation of the parasite antigens, which is necessary for the manufacture of a second-generation vaccine.

3) Vaccination of gerbils

Gerbils, receptive to infection by *B. divergens* (Lewis D. and Williams H., 1979, *Nature*, 278, 170–171) without repeated passages modifying the antigenicity or the virulence of the parasite (Murphy T. M., Gray J. S. et al., 1986, *Res. Vet. Science*, 40, 285–287), constitute a reference model for testing the efficacy of a vaccine against *B. divergens*.

a) Vaccination protocol 1

The vaccine is administered subcutaneously at two points of the back of the gerbils (average weight : 52 g) according to the following protocol:

Vaccinated animals:

| | | |
|---|---|---|
| number: 8 | 4 × 1 dose | on D0, D10, D30, D50 |
| number: 2 | 3 × 1 dose | on D0, D10, D30 |

Each dose contains 0.2 ml of parasite antigens originating from the concentration of 1.5 ml of culture supernatant from a population of 30%-parasitised human red cells, and contains 0.2 ml of saponin at a concentration of 1 mg/ml as an adjuvant.

Control animals/adjuvant: 4×1 injection
number: 2 of 400 μl of saponin on D0, D10, D30, D50 (0.5 mg/ml)
Control animals: number: 10 gerbils maintained under the same conditions of nurture as the above animals.

b) Vaccination Protocol 2

The vaccine is administered subcutaneously at two points of the back of the gerbils (average weight : 60 g) according to the following protocol:
vaccinated animals:
number: 2 2×1 dose on D0, D20

Each dose contains 0.2 ml of parasite antigens originating from the concentration of 1.5 ml of culture supernatant from a population of 30%-parasitised human red cells, and contains 0.2 ml of saponin at a concentration of 1 mg/ml as an adjuvant.

Control animals:
number: 2 gerbils maintained under the same conditions of nurture as the above animals.

c) Results

Immunoprotection against the homologous strain of B. divergens (strain Rouen 1987) (vaccination protocol 1)

On D63, the gerbils receive intraperitoneally $5.5 \times 10^4$ red cells parasitised by the homologous human strain (Rouen 1987).

The 10 unvaccinated gerbils, as well as those which have received only the adjuvant, died 6 to 9 days after contamination. The 10 vaccinated gerbils survive without ever exhibiting the slightest haemoglobinuria (clinical sign of an advanced babesiosis).

Immunoprotection against the homologous strain of B. divergens (strain Rouen 1987) (vaccination protocol 2)

On D 54, the gerbils receive intraperitoneally $1.6 \times 10^6$ red cells parasitised by the homologous human strain (Rouen 1987).

The 2 unvaccinated gerbils die 5 days after contamination. The 2 vaccinated gerbils survive without ever exhibiting the slightest haemoglobinuria.

Immunoprotection against heterologous bovine strains (protocol 1)

The above 8 gerbils which received 4 doses and were protected against the homologous strain (Rouen 1987) were contaminated once more on D79 by the intraperitoneal injection of $2.5 \times 10^7$ red cells of gerbils parasitised by heterologous strains, according to the following protocol:

| B. divergens strains used for infection | | Vaccinated animals | Control animals |
|---|---|---|---|
| Homologous strain: | | | |
| Rouen (Haute Normandie) | 1987 | 2 | 1 |
| Heterologous strains: | | | |
| Côte d'Or (Bourgogne) | 1988 | 2 | 1 |
| Indre (Centre) | 1988 | 2 | 1 |
| Loire-Atlantique (Pays de Loire) | 1988 | 2 | 1 |

The four control gerbils die between 78 and 116 hours after contamination. The 8 vaccinated gerbils survive without any haemoglobinuria.

EXAMPLE 7

Study of the cross-antigenicity between Babesia canis and Babesia divergens a) Indirect immunofluorescence The following anti-B. divergens and anti-B. canis antibodies were used on the B. divergens antigen.
gerbil anti-B. divergens serum (1)
DG7 (ascites) monoclonal antibody directed towards B. divergens (2)
anti-P35 polyclonal antibody directed towards a 35-kDa protein of B. divergens (3)
dog anti-B. canis serum (4)
monoclonal antibodies directed towards B. canis; 42E3 (5); MA3G1B11 (6)

control sera: healthy gerbil serum (7); healthy dog serum (8).

(1) and (2) proved positive with a ratio of 1/12,800.
(3) and (4) proved positive with a ratio of 1/800.
(5), (6), (7) and (8) proved negative with respect to the B. divergens antigen.

The following anti-B. divergens and anti-B. canis antibodies were used on the B. canis antigen:
dog anti-B. canis serum (1')
MA3G1B11 monoclonal antibody (2')
42E3 monoclonal antibody (3')
DG7 monoclonal antibody (4')
Gerbil anti-B. divergens serum (5')
anti-P35 polyclonal antibody (6')
control sera: healthy gerbil serum (7'); healthy dog serum (8')

The sera or antibodies (1'), (2'), (3') and (4') proved positive with a ratio of 1/4,800.

(5') proved positive with a ratio of 1/400.

(6'),(7') and (8') proved negative on the B. canis antigen.

b) Immunoprecipitations

The immunoprecipitations performed on [$^{35}$S]methionine-labelled B. divergens antigens using doganti-B. canis serum and gerbil anti-B. divergens serum demonstrated a large cross-antigenicity between the two species.

The major proteins recognised by the two types of immunoserum (dog and gerbil) have the following molecular masses:
antigen above 220 kDa
doublet of 200 to 210 kDa
doublet of 105 to 110 kDa
antigen of 85 kDa
antigen of 70 kDa
antigen of 46 kDa
antigen of 37 kDa
antigen of 35 kDa

EXAMPLE 8

Vaccination protocol 8.1) Influence of the dose fraction and the number of injections The protocol defined above is modified in the following manner:
subcutaneous vaccination
injection on D0, D21, D42
each dose contains 200 μl of parasite antigens
adjuvant: 200 μg of Quil A/injection
challenge on D63 by IP injection of $10^6$ parasitised red cells The results obtained are collated in Table 4:

TABLE 4

| | TWO INJECTIONS | | THREE INJECTIONS | |
|---|---|---|---|---|
| TREATMENT | mortality | reciprocal of the survival time | mortality | reciprocal of the survival time |
| A (1.5 ml) (equivalent)[1] | 0/10 | m = 0 es$^3$ = 0 n = 10 | 0/8 | m = 0 es = 0 n = 8 |
| B (0.3 ml) (equivalent)[1] | 1/10 | m = 0.017 es = 0.017 n = 10 | 0/8 | m = 0 es = 0 n = 8 |
| C (0.06 ml) | 10/10 | m = 0.192 es = 0.014 | 6/10 | m = 0.114 es = 0.032 |

TABLE 4-continued

| TREATMENT | TWO INJECTIONS | | THREE INJECTIONS | |
|---|---|---|---|---|
| | mortality | reciprocal of the survival time | mortality | reciprocal of the survival time |
| (equivalent)[1] | | n = 10 | | n = 10 |
| D (placebo)[2] | 8/10 | m = 0.133<br>es = 0.027<br>n = 10 | 8/8 | m = 0.203<br>es = 0.014<br>n = 10 |
| E controls (physiological solution) | 10/10 | m = 0.230<br>es = 0.08<br>n = 10 | 7/10 | m = 0.121<br>es = 0.029<br>n = 10 |

[1] ml of crude supernatant contained in a vaccinal dose
[2] culture supernatant of healthy red cells
[3] confidence interval of the mean It is seen that the supernatant according to the invention is protective at 1.5 and 0.3 ml equivalent.

8.2) Influence of the vaccinating antigenic fraction

The procedure is as above, but using various fractions corresponding to fractions 1 to 4 described above, a serum-containing supernatant, that is to say a culture with 10% serum, and a lipo supernatant, that is to say a culture containing lipoproteins.

Protection is obtained with all of these fractions.
The fractions are collated in Table 5.

TABLE 5

Results with a virulent challenge (Gerbil)

| TREATMENTS | Mortality | | Reciprocal survival time | |
|---|---|---|---|---|
| | Vaccinated | Placebo | Vaccinated | Placebo |
| Serum-containing supernatant (1.5 ml eq.) | 0/10 | 10/10 | m = 0<br>n = 10<br>es = 0 | m = 0.205<br>n = 10<br>es = 0.017 |
| Lipo supernatant (1.5 ml eq.) | 0/10 | 10/10 | m = 0<br>n = 10<br>es = 0 | m = 0.222<br>n = 10<br>es = 0.013 |
| Fraction no. 1 (1.5 ml eq.) | 0/10 | 10/10 | m = 0<br>n = 10<br>es = 0 | m = 0.205<br>n = 10<br>es = 0.013 |
| Fraction no. 2 (1.5 ml eq.) | 0/9 | 9/10 | m = 0<br>n = 9<br>es = 0 | m = 0.186<br>n = 10<br>es = 0.025 |
| Fraction no. 3 (1.5 ml eq.) | 0/9 | 8/10 | m = 0<br>n = 9<br>es = 0 | m = 0.176<br>n = 10<br>es = 0.030 |
| Fraction no. 4 (1.5 ml eq.) | 0/10 | 10/10 | m = 0<br>n = 10<br>es = 0 | m = 0.213<br>n = 10<br>es = 0.010 |

8.3) Heterologous tests

Test of heterologous protection:
subcutaneous vaccination
injections on D0, D21
each dose contains 200 μl of parasite antigens (1.5 ml of concentrated culture supernatant)
adjustment: 200 μg of Quil A/injection
challenge on D42 by IP injection of $10^6$ parasitised red cells.

TABLE 6

| Strain | Mortality | | Reciprocal of the survival time | |
|---|---|---|---|---|
| | Vaccine | Placebo | Vaccine | Placebo |
| Rouen | 0/10 | 9/10 | m = 0<br>n = 10<br>$s^2$ = 0 | m = 0.170<br>n = 10<br>$s^2$ = 0.0046 |
| German | 4/10 | 10/10 | m = 0.069<br>n = 10<br>$s^2$ = 0.0884 | m = 0.21<br>n = 10<br>$s^2$ = 0.0025 |
| English | 2/10 | 10/10 | m = 0.045<br>n = 10<br>$s^2$ = 0.0091 | m = 0.196<br>n = 10<br>$s^2$ = 0.0014 |
| 7107A | 0/10 | 8/10 | m = 0<br>n = 10<br>$s^2$ = 0 | m = 0.129<br>n = 10<br>$s^2$ = 0.0062 |
| Irish | 0/10 | 0/10 | m = 0<br>n = 10<br>$s^2$ = 0 | m = 0<br>n = 10<br>$s^2$ = 0 |

A protection is seen for heterologous strains, although the results remain average for the so-called "German" strain.

We claim:

1. Process for the culture of Babesia, characterised in that the Babesia strain is maintained in culture on a culture medium free from serum protein but containing lipoproteins as well as red cells.

2. Process according to claim 1, characterised in that the lipoproteins are of natural origin.

3. Process according to claim 2, characterised in that the lipoproteins are natural high density lipoproteins or HDL.

4. Process according to claim 2, characterised in that the lipoproteins are of human origin.

5. Process according to claim 1, characterised in that the culture medium is RPMI 1640 medium or an equivalent medium.

6. Process according to claim 1, characterised in that the medium contains, in addition, growth factors.

7. Process according to claim 1, characterised in that the HDL content is between 0.2 and 5 mg in lipid/ml.

8. Process according to claim 7, characterised in that the HDL concentration is from 0.5 to 1.5 mg in lipid/ml.

9. Process according to claim 1, characterised in that the red cells used are human red cells.

10. Process according to claim 1, characterised in that the Babesia strain is of the species *Babesia divergens*.

11. Process according to claim 1, characterised in that exoantigens soluble in the medium are recovered after culturing and they are isolated.

* * * * *